United States Patent
Richter et al.

(10) Patent No.: US 6,280,478 B1
(45) Date of Patent: Aug. 28, 2001

(54) ARTEFACT SUITABLE FOR USE AS A BONE IMPLANT

(75) Inventors: Paul Wilhelm Richter; Michael Edward Thomas, both of Pretoria (ZA)

(73) Assignee: Implico B.V., Amsterdam (NL)

(*) Notice: Subject to any disclaimer, the term of this patent is extended or adjusted under 35 U.S.C. 154(b) by 0 days.

(21) Appl. No.: 09/180,289

(22) PCT Filed: Mar. 4, 1998

(86) PCT No.: PCT/EP98/01219

§ 371 Date: Jan. 4, 1999

§ 102(e) Date: Jan. 4, 1999

(87) PCT Pub. No.: WO98/38949

PCT Pub. Date: Sep. 11, 1998

(30) Foreign Application Priority Data

Mar. 4, 1997 (ZA) .................................................. 97/1866

(51) Int. Cl.[7] .......................................................... A61F 2/28
(52) U.S. Cl. ............................................................ 623/23.56
(58) Field of Search .................................. 623/16, 17, 18, 623/23.56, 23.57, 11.11, 16.11

(56) References Cited

U.S. PATENT DOCUMENTS

| | | |
|---|---|---|
| 4,089,071 | 5/1978 | Kalnberz . |
| 4,230,455 | 10/1980 | Hidaka . |
| 4,371,484 | 2/1983 | Inukai . |
| 4,636,219 | 1/1987 | Pratt . |
| 4,839,215 | * 6/1989 | Starling et al. . |
| 4,990,163 | * 2/1991 | Ducheyne et al. . |
| 5,266,248 | 11/1993 | Ohtsuka . |
| 5,348,788 | 9/1994 | White . |

FOREIGN PATENT DOCUMENTS

| | | |
|---|---|---|
| 3042003 A1 | 7/1982 | (DE) . |
| 19610715 C1 | 6/1997 | (DE) . |
| 0338976 A1 | 10/1989 | (EP) . |
| 0526682 A1 | 2/1993 | (EP) . |
| 0677297 A1 | 10/1995 | (EP) . |
| 2427315 | 12/1979 | (FR) . |

* cited by examiner

Primary Examiner—David J Isabella
(74) Attorney, Agent, or Firm—Frommer Lawrence & Haug LLP; William S. Frommer; Marilyn M. Brogan

(57) ABSTRACT

A three-dimensional lattice structure for use as a bone implant where bone growth is required. The lattice structure has a plurality of laths or bars of bioactive material. The laths or bars cross each other in a plurality of zones, and are interconnected in these zones forming interstices between the adjacent laths or bars. The interstices define a plurality of interconnected pored or channels in the lattice structure.

9 Claims, 2 Drawing Sheets

ARTEFACT SUITABLE FOR USE AS A BONE IMPLANT

Figure 1:
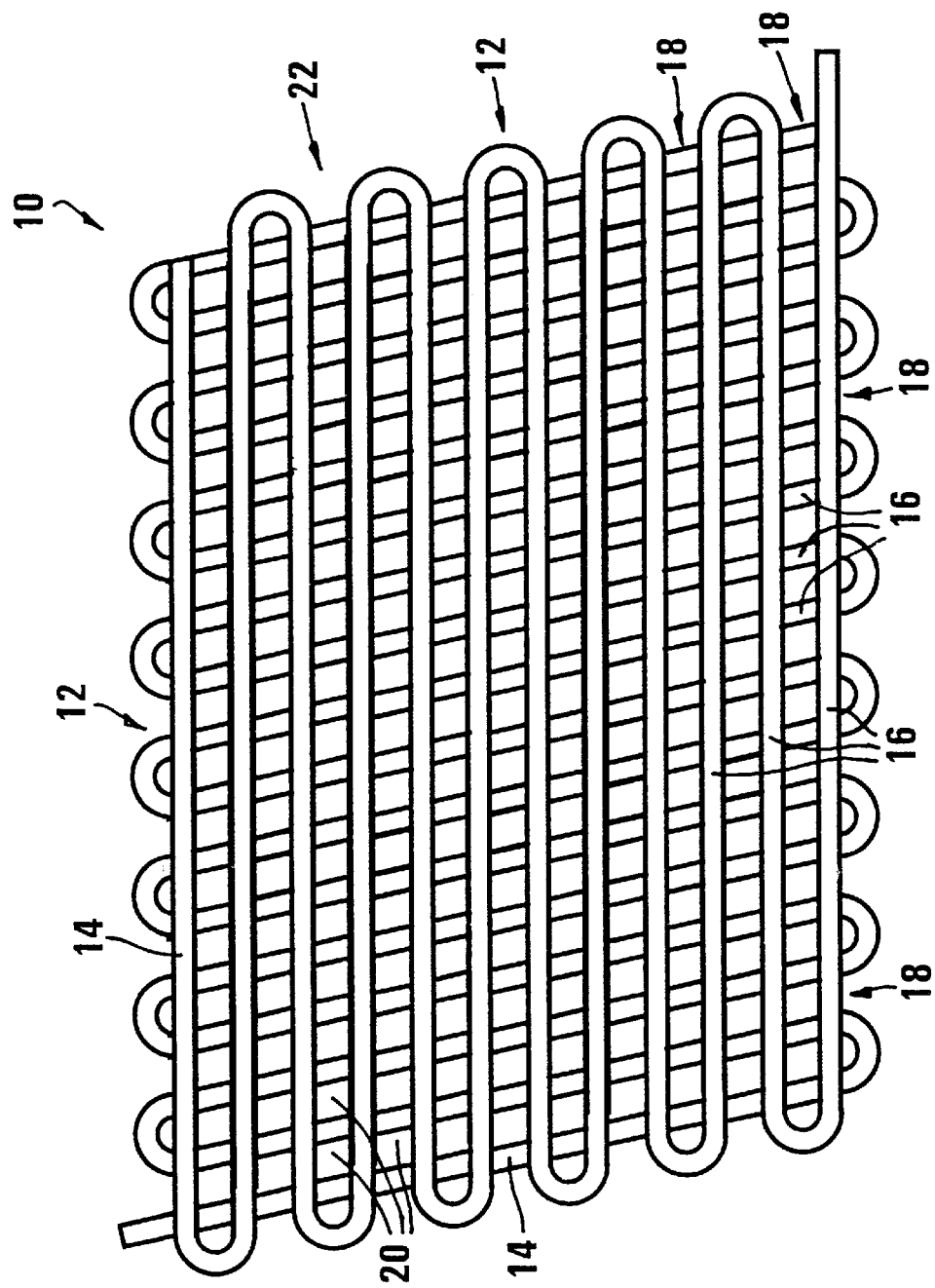

This invention relates to an artefact suitable for use as a bone implant by implantation thereof into a subject at a body site where bone growth is required. It relates also to a method of making such artefact.

According to a first aspect of the invention, there is provided an artefact suitable for use as a bone implant by implantation thereof into a subject at a body site where bone growth is required, the artefact comprising a three-dimensional lattice structure having a plurality of laths or bars of bioactive material crossing each other in a plurality of zones and interconnected in said zones, with interstices thus being provided between adjacent laths or bars, these interstices defining a plurality of interconnected pores or channels in the lattice structure.

The porous three-dimensional lattice structure thus, in use, permits bone growth into its porous spaces, thereby to secure its incorporation into and osteointegration with the surrounding viable bone at the margins of a bone defect at the site where the artefact is implanted. The lattice structure may thus be osteoconductive, ie permitting bone growth into its porous spaces when it is in direct contact with viable bone, and/or it may be osteoinductive, ie permitting bone growth at its porous spaced independently of the presence of viable bone in contact with the artefact.

The interconnected pores or channels should, for enhanced osteoinductive or osteoconductive compatibility, comprise from 30% to 80% of the total volume of the artefact.

The external surfaces of the laths, bars or rods making up the lattice structure may be smooth. Instead, however, the external surfaces of at least some of the bars or rods may be provided with surface features, such as indentations therein. The indentations, when present, may be of hemispherical, concave or irregular shape.

The bioactive material of the bars or rods may be a sintered ceramic or glass material having low or no porosity. In particular it may be a calcium phosphate-based ceramic material such as hydroxylapatite or tricalcium phosphate.

The porous lattice structure may comprise an extrudate of the bioactive material, with the bars or rods having been formed from extruded strands of the bioactive material, which strands are thus arranged or stacked and consolidated into at least part of the intimately bound three-dimensional open or porous lattice structure.

Thus, according to a second aspect of the invention, there is provided a method of making an artefact suitable for use as a bone implant by implantation thereof into a subject at a body site where bone growth is required, the method comprising extruding an extrudable mixture of a bioactive material in particulate form and an organic base, into a three-dimensional lattice structure having a plurality of laths or bars formed from extruded strands of the mixture, the laths or bars crossing each other in a plurality of zones, so that interstices are provided between adjacent laths or bars and these interstices define a plurality of interconnected pores or channels in the lattice structure;

removing the organic base, to form a green artefact; and heating the green artefact to a temperature sufficient to sinter the bioactive material and to fuse the bars or laths in said zones where they cross.

It will be appreciated that the extrusion of the mixture into the three-dimensional lattice structure need not necessarily be effected in one step or operation but can instead be effected in a number of steps or stages. Thus, for example, the extrudable mixture can initially be extruded onto filaments which can thereafter be arranged into the lattice structure.

The method may include, if desired, forming surface features such as indentations in or on the external surfaces of the bars or laths prior to sintering the green artefact eg as the lattice structure is formed.

The extrusion of the extrudable mixture and the formation of the lattice structure can be effected using known apparatus such as known apparatus for injection moulding of particulate materials, known apparatus for solid free form manufacture by means of fused deposition moulding of ceramics, known apparatus for three-dimensional printing of ceramics, known apparatus for multiphase jet solidification of ceramics, and/or known apparatus for stero lithography.

The bioactive material may be in powdered form initially eg may be powdered hydroxylapatite. The organic base is a binder which serves as a temporary vehicle to allow processing of the hydroxylapatite powder. The base may be a single component substance, or may be made up of multiple components and additives. The base or binder can thus be selected so that it influences the flow characteristics of the extrudable mixture, permits interaction and/or agglomeration of the powder, influences the rheology of the mixture, influences the moulding capabilities of the mixture, and permits ready removal or debonding thereof. The binder may thus comprise a mixture of two or more of the following: a lubricant, a polymer, an elastomer, a wax and a tacktifier.

The removal of the organic base may be by solvent extraction and/or by a thermal process.

According to a third aspect of the invention, there is provided a method of making an artefact suitable for use as a bone implant by implantation thereof into a subject at a body site where bone growth is required, the method comprising extruding an extrudable mixture of a bioactive material in particulate form and an organic base, into a lattice component having a plurality of laths or bars formed from extruded strands of the mixture, with spaces or interstices provided between adjacent laths or bars;

removing the organic base;

either before or after removal of the organic base arranging a plurality of the lattice components into a three-dimensional lattice structure wherein the spaces or interstices of the lattice components define a plurality of interconnected pores or channels in the lattice structure; and heating the resultant green artefact to a temperature sufficient to sinter the bioactive material and to fuse the bars or laths in zones where they cross.

As described hereinbefore, the extrusion of the mixture into the lattice components need not necessarily be effected in one step or operation but can instead be effected in a number of steps or stages. Thus, the extrudable mixture can initially be extruded into filaments, which can thereafter be arranged into the lattice components. Each lattice component can then, for example, comprise a single or continuous filament arranged in a plurality of the bars or laths. Instead, however, each lattice component can comprise a plurality of filaments each defining one or more of the bars or laths.

The bars or laths in each lattice component may extend parallel to one another.

The invention will now be described by way of example, with reference to the accompanying diagrammatic drawings.

In the Drawings

Figure 2:
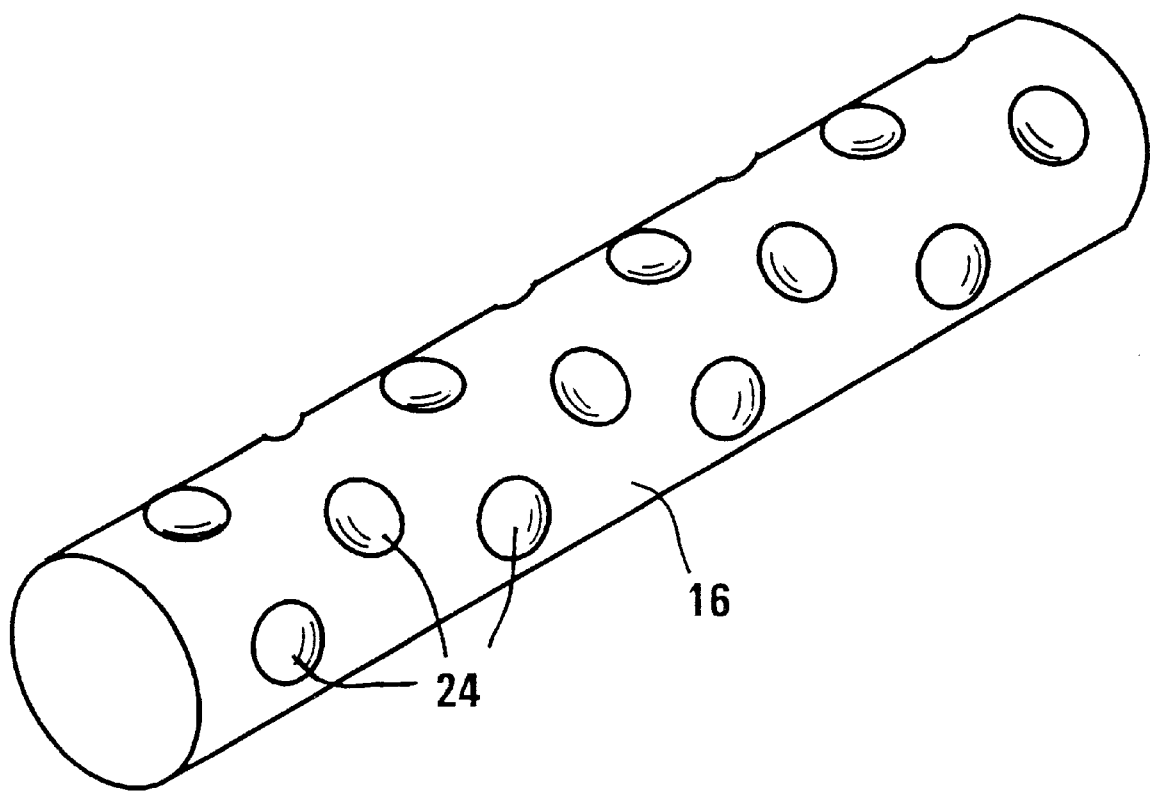

FIG. 1 shows a plan view of part of an artefact, according to the invention, which is suitable for use as a bone implant by implantation thereof into a subject at a body site where bone growth is required; and FIG. 2 is an enlarged three-dimensional view of part of one of the bars or laths of the artefact of FIG. 1.

In the drawings, reference numeral 10 generally indicates an artefact suitable for use as a bone implant by implantation thereof into a subject at a body site where bone growth is required.

The artefact 10 comprises a plurality of lattice components, each generally indicated by reference numeral 12. The lattice components 12 are thus located one above the other in abutting relationship. Each lattice component 12 comprises a single strand 14 of substantially non-porous or solid hydroxylapatite arranged or formed into a plurality of parallel bars or laths 16. The bars or laths 16 of one lattice component 12 extend orthogonally to those of an adjacent lattice component 12. However, in other versions (not shown) the laths 16 of one lattice component 12 can extend at any angle between 10° and 90° relative to those of an adjacent component. In this fashion, spaces or interstices 18 between adjacent bars or laths 16 of the lattice components define a plurality of interconnected pores or channels 20 in the three-dimensional lattice structure 22 made up of the plurality of lattice components 12. The bars or laths 16 are connected together or fused together in the zones where they cross.

If desired, the outer surfaces of at least some of the bars or laths can be provided with indentations 24, as shown in FIG. 2. It will be appreciated that these indentations can have any other desirable shape eg be hemispherical, concave or of irregular shape.

The artefact 10 can be formed in accordance with one of the following non-limiting examples:

EXAMPLE 1

An organic binder base or material is prepared by admixing 44 volume percent ethylene vinyl acetate such as that available under the Trade Mark Elvax 210W; 50 volume percent polyolefin wax such as that available under the Trade Mark Hostamont TP EK 583; 3 volume percent stearic acid; and 3 volume percent plasticizer, such as that available under the Trade Mark Sancticizer 261. The mixture is prepared by admixing the components in a z-blade mixer. To this mixture is gradually added sufficient hydroxylapatite ceramic powder to make up a mixture comprising 56 volume percent of a ceramic powder and 44 volume percent of the organic binder material. The mixture is heated to 150° C. with continuous mixing, to obtain a homogeneous material. The mixture is cooled to room temperature, and then granulated to provide an extrudable feedstock. The granulated feedstock is extruded as continuous filaments at a temperature between 110° C. and 130° C. by means of a computer controlled apparatus that allows movement in the x-y-z directions, to build up an open three-dimensional layered lattice structure.

For example, the open three-dimensional layered lattice structure may be formed using solid freeform fabrication (SFF) techniques. These techniques involve making three-dimensional components directly from computer-aided design (CAD) files. Examples of such SFF techniques include laminated object manufacturing (LOM), three-dimensional printing, fused deposition of ceramics (FDC), and fused deposition modelling (FDM—trademark). SFF techniques such as FDC and FDM involve building the artefact layer-by-layer from a CAD file. Continuous filaments of the binder/hydroxylapatite mixture are fed into a liquefier head by means of computer-driven rollers. The liquefier head is machine controlled to move in a horizontal or platform moves in the z-direction, to complete the three-axis movement and hence the artefact. Molten mixture is extruded out of a nozzle at the end of the liquefier, to form the artefact. Typically, the 3-D Modeler system available from Stratasys, Inc of Eden prairie, Minnesota, USA, can be used.

The extruded filaments or strands are thus of uniform diameter, typically between 0.2 mm and 2 mm in diameter. The filaments are thus laid down to form a single layered lattice component of the desired width and breadth and consisting of parallel strands or laths spaced 0.2 mm to 2 mm apart. This lattice component is then covered by another similar layered lattice component, but with the strands of this lattice component being at an angle between 10° and 90° to those of the first lattice component. This process is repeated until the resultant lattice structure has the desired height or thickness. The green artefact thus formed is heated to remove the organic material, by slow heating it in a furnace from room temperature to 600° C. at a rate not exceeding 40°/hour. Thereafter, the lattice structure is sintered at 1250° C. for 3 hours to form the artefact in which the bars or laths of the lattice components are fused together in the zones where they cross.

EXAMPLE 2

An organic binder material is made up by mixing 99 mass percent polyolefin elastomer such as that available under the Trade Mark Engage EG8150; 0.5 mass percent polyethylene wax such as that available under the Trade Mark PE520 from Hoechst SA (Proprietary) Limited; and 0.4 mass percent internal lubricant such as glycerol monostearate, in a z-blade mixer. To this mixture is gradually added sufficient hydroxylapatite ceramic powder to make up a mixture comprising 56 volume percent ceramic powder and 44 volume percent organic binder. The mixture is heated to 130° C. with continuous mixing, to obtain a homogeneous material. The material is cooled to room temperature, and granulated to produce a feedstock. The granulated feedstock is extruded into filaments having a homogeneous diameter of between 1 mm and 2 mm. The filaments are fed into a computer controlled FDC (fuse deposition of ceramics) apparatus to produce a lattice structure. This is effected by laying down the filaments in a layered lattice component consisting of parallel bars or laths of the filaments spaced 0.1 mm to 2 mm apart. Thereafter, further similar layered lattice components are laid down on the first lattice component, with the direction of deposition of the filaments in adjacent lattice components extending at an angle between 10° to 90° to those of the preceding layer.

The resultant lattice structure is heated and sintered as described in Example 1.

EXAMPLE 3

The binder material is prepared as in Example 1. The filaments are extruded and arranged in lattice components as described in Example 1, except that during extrusion of filaments indentations are made on the filaments prior to the filaments being laid down. The indentations are 0.2 mm to 2 mm wide, and can be hemispherical, concave or of irregular shape. The resultant lattice structure is heated and sintered as described in Example 1.

It is known that porous bioactive ceramics such as porous hydroxylapatite with suitable microstructure and connected porosity, are useful as bone substitutes when implanted in a living body, since new bone generation and ingrowth into the structure readily occurs. In particular, when certain geometric features are incorporated on the surfaces of or in such materials, such as spherical open concavities of diameter 200 microns to 3000 microns, a particularly suitable substrate which is capable of inducing new bone formation at the site where the material is implanted, is obtained. Thus, with such features, this material exhibits intrinsic osteoinductivity.

It is believed that the artefact according to the invention which has a three-dimensional open lattice or grid structure of ceramic material will also exhibit intrinsic osteoinductive activity due to its chemical composition and the micro/macro structure of the surfaces of the bars or laths making up the lattice structure.

Furthermore, porous ceramic structures have, generally, decreased mechanical strength compared to solid or monolithic ceramic structures. However, a high degree of porosity, ie a high percentages of pores in the porous structure, as well as a large number of pores ie pores of as small a size as is feasible so as to have a large number of small pores rather than a small number of large pores, are desirable for bone growth. However, as the number of pores and the porosity increases, the strength decreases, so that biomaterial comprising only porous hydroxylapatite normally cannot be used in load bearing applications. It is believed that the implants according to the invention provide the necessary mechanical strength while having a desired degree of porosity as well as a desired number of pores. Thus, the implants according to the invention encourage new bone growth, have adequate mechanical strength since the bars or laths are of substantially solid hydroxylapatite, and allow bone ingrowth since the lattice structure has fully connected three-dimensional pores and channels therein.

Additional advantages which the artefacts according to the invention provide include:

the artefacts 10 are highly reproducible, since their physical features do not arise from processes such as foaming or decomposition which are traditionally used in the manufacture of porous materials, but are specifically designed and engineered the pore or channels sizes, mechanical strength of the lattice structure, and directional properties of the lattice structure, can readily be modified or optimised for particular applications during manufacture of the lattice structures, it is possible to extend the lattice structures by protrusions such as pins or end caps which are useful in locating or fixing the position of the implant relative to that of natural bone at a defect site it is possible to minimize or prevent edge chipping or fracture due to bending of the lattice structure, which is a common fault in ceramics, by using continuous curved shape in respect of the bars or laths, especially at the edges of the lattice structure it is possible to introduce hemispherical cavities or indentations on the surfaces of the bars or rods making up the lattice structure. Such cavities or indentations are known to impart osteoinduction and enhance the biological response around the structure.

What is claimed is:

1. An artifact suitable for use as a bone implant by implantation thereof into a subject at a body site where bone growth is required, the artifact comprising a three-dimensional lattice structure having a plurality of bars of bioactive material crossing each other in a plurality of zones and being fused in said zones, with interstices thus being provided between adjacent bars, these interstices defining a plurality of interconnected pores or channels in the lattice structure.

2. An artifact according to claim 1, wherein the bars are in the form of sintered extruded strands of the bioactive material, and wherein the lattice structure is osteoconductive and osteoinductive.

3. An artefact according to claim 1, wherein the interconnected pores or channels of the lattice structure comprise from 30% to 80% of the total volume of the artefact.

4. An artifact according to claim 1, wherein the external surfaces of at least some of the bars or rods have hemispherical or concave indentations therein.

5. An artifact according to claim 1, wherein the bioactive material of the bars or rods is hydroxylapatite or tricalcium phosphate.

6. An artifact suitable for use as a bone implant by implantation thereof into a subject at a body site where bone growth is required, the artifact comprising a three-dimensional lattice structure having a plurality of bars in the form of sintered extruded strands of bioactive material, the bars crossing each other in a plurality of zones and being fused in said zones, with interstices thus being provided between adjacent bars, and these interstices defining a plurality of interconnected pores or channels, and with the lattice structure being osteoconductive and osteoinductive.

7. An artifact according to claim 6, wherein the interconnected pores or channels of the lattice structure comprise from 30% to 80% of the total volume of the artifact.

8. An artifact according to claim 6, wherein the external surfaces of at least some of the bars or rods have hemispherical or concave indentations therein.

9. An artifact according to claim 6, wherein the bioactive material of the bars or rods is hydroxylapatite or tricalcium phosphate.

* * * * *